(12) United States Patent
Carlson et al.

(10) Patent No.: US 8,546,617 B1
(45) Date of Patent: Oct. 1, 2013

(54) DIOXABORINANES AND USES THEREOF

(75) Inventors: William B. Carlson, Seattle, WA (US); Gregory D. Phelan, Cortland, NY (US)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 13/554,783

(22) Filed: Jul. 20, 2012

(51) Int. Cl.
*C07F 5/02* (2006.01)
*C08K 5/55* (2006.01)

(52) U.S. Cl.
USPC .............................................. 568/6; 524/108

(58) Field of Classification Search
None
See application file for complete search history.

(56) References Cited

U.S. PATENT DOCUMENTS

| | | | |
|---|---|---|---|
| 3,025,274 | A | 3/1962 | Thomas et al. |
| 4,608,440 | A | 8/1986 | Saischek et al. |
| 4,778,833 | A | 10/1988 | Van der Drift et al. |
| 5,521,165 | A | 5/1996 | Warren et al. |
| 5,633,236 | A | 5/1997 | Warren et al. |
| 2005/0013939 | A1 | 1/2005 | Vinden et al. |
| 2009/0253879 | A1 | 10/2009 | Nishio et al. |

FOREIGN PATENT DOCUMENTS

| | | |
|---|---|---|
| GB | 0 901 567 | 7/1962 |
| JP | 2006-124639 | 5/2006 |
| JP | 2006-309120 | 11/2006 |

OTHER PUBLICATIONS

Meinhold, R. H., "Aromatic Boronic Acids as Wood Preservatives, Including Solid State NMR Studies," Jun. 1993, *Ind. Res. Ltd. Rep.*, No. 89, 42 pp.
Aldrich Chemistry "Handbook of Fine Chemicals," Australian/ New Zealand Edition, 2009-2010, pp. 71, 569, 1515, 2079 and 2706.
Bebernitz, G.R., et al., "Reduction in glucose levels in STZ diabetic rats by 4-(2,2-dimethyl-1-oxopropyl)benzoic acid: a prodrug approach for targeting the liver" Feb. 2001, J Med Chem, vol. 4, No. 4, pp. 512-523.
CAS RN 1141927-92-5, STN Entry Date May 3, 2009.
CAS RN 54383-83-4, STN Entry Date Nov. 16, 1984.
CAS RN 84063-31-0, STN Entry Date Nov. 16, 1984.
CAS RN 84063-33-2, STN Entry Date Nov. 16, 1984.
CAS RN 886974-32-9, STN Entry Date Jun. 6, 2006.
CAS RN 914100-80-4, STN Entry Date Nov. 28, 2006.
David, S., "The anomalous reactivity of the bis(dibutylstannylene) acetal of pentaerythritol: a case of triple activation," 2001, Carbohyd. Res., vol. 331, pp. 327-329.
International Search Report and Written Opinion received for PCT/US/2012/030315 mailed Jun. 6, 2012.
Mallinckrodt Baker, Inc., "Material Safety Data Sheet: Sodium Benzoate," Effective Date: Aug. 17, 2009, retrieved from http://www.jtbaker.com/jsds/englishhtml/s2930.htm, 4 pages.
Meinhold, R. H., "Aromatic boronic acids as wood preservatives, including solid state NMR studies," 1993, Ind. Res. Ltd. Rep., (89), 80 pages.
Miyaura, N., et al., "Palladium-Catalyzed Cross-Coupling Reactions of Organoboron Compounds," Nov. 1995, Chem. Rev., vol. 95, No. 7, pp. 2457-2483.
Miyaura, N., et al., "Stereoselective synthesis of arylated (E)-alkenes by the reaction of alk-1-enylboranes with aryl halides in the presence of palladium catalyst," 1979, J. Chem. Soc., Chem. Commun., Issue 19, pp. 866-867.
Murata, M., et al., "Synthesis of benzylboronates via palladium catalyzed borylation of benzyl halides with pinacolborane," 2002, Synthetic Commun, vol. 32, No. 16, pp. 2513-2517.
Rasset-Deloge, C., et al., "ChemInform: Synthesis of Vinylboronates 3B2-Substituted by an Electron-Withdrawing Group: A New Class of Electron-Poor Olefins," Jan. 12, 1993, ChemInform, vol. 24, Issue 2, pp. 285-290.
Rose Mill Chemicals & Lubricants, "Material Safety Data Sheet: Borax 5 mol," Revised Apr. 4, 2009, retrieved from http://www.rosemill.com, 2 pages.
Schunicht, C., et al., "ChemInform: Microgel-Supported Oxazaborolidines: Novel Catalysts for Enantioselective Reductions," Jun. 27, 2000, ChemInform, vol. 31, Issue 26, pp. 1693-1699.
Sciencelab.com, Inc., "Material Safety Data Sheet: Pentaerythritol MSDS," printed on Jun. 19, 2012, retrieved from http://www.sciencelab.com, 5 pages.
Voloshin, Y.Z. et al., "Application of the allylboration reaction of terminal acetylenes with allyldihaloboranes for the preparation of capping agents for the synthesis of precursors of polymeric iron(II) clathrochelates," Nov. 2006, Russian Chemical Bulletin, vol. 55, No. 11, pp. 1971-1981.
Wulff, G., et al., "Enzyme-Analogue Built Polymers, 23. Influence of the Structure of the Binding Sites on the Selectivity for Racemic Resolution," Makromol. Chem 1987, vol. 188, pp. 741-748.
Wulff, G., et al., "Über enzymanalog gebaute polymer, 16. Über den Einfluβ der flexibilität der haftgruppen auf die racemattrennungsfähigkeit," Die Makromolekulare Chemie, Oct. 18, 1982, vol. 183, Issue 10, pp. 2469-2477.
Wulff, G., et al., "Über enzymanalog gebaute Polymere, III. Zur Synthese von polymerisierbaren D-Glycerinsäurederivaten," Chemische Berichte, vol. 107, Issue 10, Oct. 1974, pp. 3364-3376.

(Continued)

*Primary Examiner* — Kamal Saeed
(74) *Attorney, Agent, or Firm* — Foley & Lardner LLP

(57) ABSTRACT

A dioxaborinane compound, or salt thereof, where boron has two oxy substituents, each independently substituted with H, alkyl, alkenyl, aryl, —C(O)R$^3$, —C(O)OR$^3$, —C(O)NHR$^3$, or the two oxy substituents, together with the oxygen atoms to which they are bonded, join to form a 5- or 6-membered ring; and R$^3$ is H, alkyl, alkenyl, or aryl, where the alkyl and alkenyl are optionally interrupted with one or more oxygen or sulfur atoms; and where boron also has the substituent -L-X$^1$-PG$^1$; where L may be absent, or alkylenyl, alkenylenyl, or arylene, where the alkylenyl and alkenylenyl are optionally interrupted with one or more oxygen or sulfur atoms; X$^1$ is absent, or is amino, oxo, thio, or phosphino; and PG$^1$ is a polymerizable group. The dioxaborinane compound can be used as a wood preservative.

19 Claims, No Drawings

(56) References Cited

OTHER PUBLICATIONS

Yang, C. "Alkylboronic Esters from Copper-Catalyzed Borylation of Primary and Secondary Alkyl Halides and Pseudohalides," Jan. 9, 2012, Angewandte Chemie International Edition, vol. 51, Issue 2, pp. 528-532.

Avantor Material Safety Data Sheet for Sodium Benzoate, Version 1, Revision date Dec. 12, 2011 as downloaded on Apr. 2, 2013 from http://www.avantormaterials.com/documents/MSDS/usa/English/S2930_msds_us_cov_Default.pdf, 6 pp.

Butler, D.N. et al., "Attempted Synthesis of 2,4-Dihydroxy-4,3-borazaropyridine. Preparation of Aminoalkylboronic Acids," *J. Med. Chem.*, 1966, vol. 9, No. 3 pp. 362-365.

Butler, D.N., et al., "Monohydroboration of N-Alkenylcarbamates; Preparation of Aminoalkylboronic Acids," Chemical Communications, 1965, No. 15, p. 333.

Rose Mill Chemicals and Lubricants Material Safety Data Sheet for Borax Pentahydrate, Revised Apr. 4, 2009, as downloaded on Apr. 2, 2013 from http://www.rosemill.com/v/html/msds/chem_borax5_mol_msds.pdf, 2 pp.

Yalinkilic, M.K., et al., "Enhancement of the biological resistance of wood by phenylboronic acid treatment," *Journal of Wood Science*, 1998, vol. 44, No. 2, pp. 152-157.

DIOXABORINANES AND USES THEREOF

CROSS-REFERENCE TO RELATED APPLICATIONS

This application claims the benefit of International Application Serial No. PCT/US2012/030315, filed on Mar. 23, 2012, the entire disclosure of which is hereby incorporated by reference for all purposes in its entirety as if fully set forth herein.

FIELD

The present technology relates to dioxaborinane compounds for use as wood preservatives.

BACKGROUND

The following description is provided to assist the understanding of the reader. None of the information provided or references cited is admitted to be prior art to the present technology.

Wood preservatives are used to deter or kill organisms that degrade wood (e.g., wood bearings, utility poles, railroad ties, landscape timbers, docking and marine structures). Many such conventional wood preservatives such as heavy metals or copper naphthenates are fully toxic to wood destroying organisms (e.g., bacteria, fungi, wood boring beetles, termites, marine organisms, and animals such as rodents), but have the disadvantage of also being generally toxic to the environment.

Further, to be most effective, wood preservatives must penetrate into the wood interior. To do so, many wood preservatives are formulated as liquids that are impregnated into wooden structures. The liquids typically remain fluid even after they are forced into the wood and are thus prone to leakage from the wood. Leakage of toxic wood preservatives impacts the environment and can raise maintenance costs due to the need for additional labor and materials for the upkeep necessary to reprotect wooden structures.

For example, when stored horizontally, wooden structures such as utility poles and railroad ties need to be turned periodically to prevent the fluid wood preservatives in the wood from being forced down and out of the utility poles by gravity. Further, fluid migration may leave installed wooden products unprotected, at the expense of the surrounding environment, as may be seen in telephone poles where the impregnated fluid has migrated downward and left the top dry and vulnerable. There is thus a need for an improved preservation technology based upon wood preservatives that are less susceptible to migration from the wood that is being preserved. There is a further need for an improved preservation technology based upon wood preservatives that include environmentally friendly materials.

SUMMARY

The present technology provides for compounds having a pendant dioxaborinane moiety that deters or kills organisms that degrade wood, and a polymerizable moiety that allows the compound to be polymerized in situ after being impregnated into wood products. As such, the compound is effectively fixed within treated wood to deter seepage from the wood and minimize environmental risks.

Processes for treating wood and wood products with the compound having a pendant dioxaborinane moiety are also provided. Wood is coated or impregnated under pressure with the compound having a pendant dioxaborinane moiety, which compound is polymerized on the surface of the wood and/or within the interior of the wood. Whether the wood is surface treated or impregnated, the polymerized compound is effectively fixed. Optionally, pressure and vacuum may be applied in selected sequence to promote impregnation, and heat, blowing air, oxygen, ultraviolet light, and other agents may be employed to promote polymerization of the compound used to surface-treat or impregnate the wood. Additional additives may be used to prevent pest infestations and the growth of fungi, or to promote the migration of the compound having a pendant dioxaborinane moiety into the wood.

In one aspect, a compound is provided as represented by Formula I, or a salt thereof:

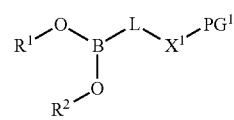

I

In Formula I, L may be absent, or alkylenyl, alkenylenyl, or arylene, where the alkylenyl and alkenylenyl are optionally interrupted with one or more oxygen or sulfur atoms; $X^1$ is absent, or is amino, oxo, thio, or phosphino; $PG^1$ is a polymerizable group; $R^1$ and $R^2$ are independently H, alkyl, alkenyl, aryl, —C(O)$R^3$, —C(O)O$R^3$, —C(O)NH$R^3$, or $R^1$ and $R^2$ together with the oxygen atoms to which they are bonded join to form a 5- or 6-membered ring; and $R^3$ is H, alkyl, alkenyl, or aryl, where the alkyl and alkenyl are optionally interrupted with one or more oxygen or sulfur atoms.

In another aspect, the compound of Claim 1 is of Formula IA:

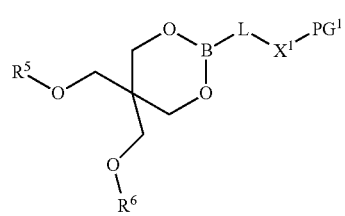

IA

In Formula IA, $R^5$ and $R^6$ are independently H, alkyl, alkenyl, aryl, or —C(O)$R^7$; and $R^7$ is alkyl, alkenyl, or aryl. In certain embodiments, $R^5$ is —C(O)alkyl and $R^6$ is —C(O)alkyl. In other embodiments, $R^5$ is —C(O)($C_{15}$-$C_{20}$ alkyl) and $R^6$ is —C(O)($C_{15}$-$C_{20}$ alkyl).

In yet another aspect, a polymer is provided that includes a polymerization product of the compound as represented by Formula I. In certain embodiments, the polymer has a weight average molecular weight of about 5,000 to about 2,000,000 g/mol.

In another aspect, a composition is provided that includes the compound as represented by Formula I and a cellulosic material. In certain embodiments, the composition includes cellulosic material that is wood, and the composition is a wood-polymer borinane composite material.

In another aspect, a process is provided of preparing a wood-polymer borinane composite material comprising the steps of: contacting a cellulosic material with a compound as represented by Formula I; and polymerizing the compound as represented by Formula I to form the wood-polymer borinane composite material.

In another aspect, a method is provided of preparing a compound as represented by Formula I, the method including a first step of contacting a compound of Formula II with a compound of Formula III to form the compound of Formula I where Formula I is:

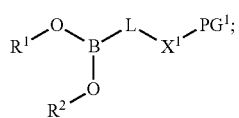

Formula II is:

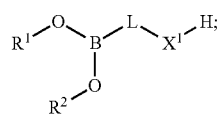

and
Formula III is $PG^1$-Y.

In the above Formulas I and III, L is absent, or is alkylenyl, alkenylenyl, or arylene, where the alkylenyl and alkenylenyl are optionally interrupted with one or more oxygen or sulfur atoms; $X^1$ is absent, or is —O—, —NH—, —S—, or —P($R^3$)—; $R^1$ and $R^2$ are independently H, alkyl, alkenyl, aryl, —C(O)$R^3$, —C(O)O$R^3$, —C(O)NH$R^3$, or $R^1$ and $R^2$ together with the oxygen atoms to which they are bonded join to form a 5- or 6-membered ring; $R^3$ is H, alkyl, alkenyl, or aryl, where the alkyl and alkenyl are optionally interrupted with one or more oxygen or sulfur atoms; $PG^1$ is acrylyl, methacrylyl, epoxyl, isocyanyl, styrenyl, vinyl, oxyvinyl, thiovinyl, ketovinyl, ketoalkyl, ketoalkoxy, ketoaryl, or cycloalkenyl; and $Y^1$ is a leaving group.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

The illustrative embodiments described in the detailed description and claims are not meant to be limiting. Other embodiments may be utilized, and other changes may be made, without departing from the spirit or scope of the subject matter presented here.

The present technology is described herein using several definitions, as set forth throughout the specification.

As used herein, unless otherwise stated, the singular forms "a," "an," and "the" include plural reference. Thus, for example, a reference to "a cell" includes a plurality of cells, and a reference to "a molecule" is a reference to one or more molecules.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Alkyl groups include straight chain, branched chain, or cyclic alkyl groups having 1 to 24 carbons or the number of carbons indicated herein. In some embodiments, an alkyl group has from 1 to 16 carbon atoms, from 1 to 12 carbons, from 1 to 8 carbons or, in some embodiments, from 1 to 6, or 1, 2, 3, 4 or 5 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. In some embodiments, the alkyl groups may be substituted alkyl groups.

Cycloalkyl groups are cyclic alkyl groups having from 3 to 10 carbon atoms. In some embodiments, the cycloalkyl group has 3 to 7 ring members, whereas in other embodiments the number of ring carbon atoms range from 3 to 5, 3 to 6, or 5, 6 or 7. Cycloalkyl groups further include monocyclic, bicyclic and polycyclic ring systems. Monocyclic groups include, e.g., cyclopropyl, cyclobutyl, cyclopentyl, cyclohexyl, and cycloheptyl groups. Bicyclic and polycyclic cycloalkyl groups include bridged or fused rings, such as, but not limited to, bicyclo[3.2.1]octane, decalinyl, and the like. Cycloalkyl groups include rings that are substituted with straight or branched chain alkyl groups as defined above. In some embodiments, the cycloalkyl groups are substituted cycloalkyl groups. Representative substituted alkenyl groups may be mono-substituted or substituted more than once, such as, but not limited to, mono-, di- or tri-substituted with substituents such as those listed above. Representative substituted alkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have from 2 to 24 carbon atoms, and typically from 2 to 10 carbons or, in some embodiments, from 2 to 8, 2 to 6, or 2 to 4 carbon atoms. Examples include, but are not limited to vinyl, allyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, among others. Representative substituted alkenyl groups may be mono-substituted or substituted more than once, such as, but not limited to, mono-, di- or tri-substituted with substituents such as those listed above.

The terms "alkylene," "cycloalkylene," and "alkenylene," alone or as part of another substituent means a divalent radical derived from an alkyl, cycloalkyl, or alkenyl group, respectively, as exemplified by —CH$_2$CH$_2$CH$_2$CH$_2$—. For alkylene, cycloalkylene, and alkenylene linking groups, no orientation of the linking group is implied.

The term "amine" (or "amino") as used herein refers to —NHR and —NRR' groups, where R, and R' are independently hydrogen, or a substituted or unsubstituted alkyl, alkenyl, alkynyl, cycloalkyl, aryl or aralkyl group as defined herein. Examples of amino groups include —NH$_2$, methylamino, dimethylamino, ethylamino, diethylamino, propylamino, isopropylamino, phenylamino, benzylamino, and the like.

The term "oxo" refers to a divalent oxygen group. While the term includes doubly bonded oxygen, such as that found in a carbonyl group, as used herein, the term oxo explicitly includes singly bonded oxygen of the form —O— which is part of a polymer backbone. Thus, an oxo group may be part of an ether linkage (—O—), an ester linkage (—O—C(O)—), a carbonate linkage (—O—C(O)O—), a carbamate linkage (—O—C(O)NH— or —O—C(O)NR—), and the like.

"Substituted" refers to a chemical group as described herein that further includes one or more substituents, such as lower alkyl (including substituted lower alkyl such as haloalkyl, hydroxyalkyl, aminoalkyl), aryl (including substituted aryl), acyl, halogen, hydroxy, amino, alkoxy, alkylamino, acylamino, thioamido, acyloxy, aryloxy, aryloxyalkyl, carboxy, thiol, sulfide, sulfonyl, oxo, both saturated and unsaturated cyclic hydrocarbons (e.g., cycloalkyl, cycloalkenyl), cycloheteroalkyls and the like. These groups may be attached to any carbon or substituent of the alkyl, alkenyl, alkynyl, aryl, cycloheteroalkyl, alkylene, alkenylene, alkynylene, arylene, hetero moieties. Additionally, the substituents may be pendent from, or integral to, the carbon chain itself.

The terms "wood" or "wood product" include any wood and wood-based materials, including but not limited to wood bearings, utility poles, railroad ties, landscape timbers, docking and marine structures, logs, dried lumber, green lumber, fiberboards, strand board, laminated veneer lumber, wood composites, cellulosic composites, plastic wood composites, and engineered wood formed from wood chips. The wood may be softwood or hardwood. The softwood may include pine species and spruce species, for example, heartwood or sapwood.

The present technology provides for compounds having a pendant dioxaborinane moiety that deters or kills organisms that degrade wood, and a polymerizable moiety that allows the compound to be polymerized in situ after being impregnated into wood or wood products. As such, the compound is effectively fixed within treated wood to deter seepage from the wood and minimize environmental risks.

In one aspect, a compound is provided as represented by Formula I, or a salt thereof:

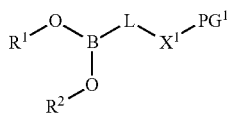

I

In Formula I, L may be absent, or alkylenyl, alkenylenyl, or arylene, where the alkylenyl and alkenylenyl are optionally interrupted with one or more oxygen or sulfur atoms; $X^1$ is absent, or is amino, oxo, thio, or phosphino; $PG^1$ is a polymerizable group; $R^1$ and $R^2$ are independently H, alkyl, alkenyl, aryl, —C(O)$R^3$, —C(O)O$R^3$, —C(O)NH$R^3$, or $R^1$ and $R^2$ together with the oxygen atoms to which they are bonded join to form a 5- or 6-membered ring; and $R^3$ is H, alkyl, alkenyl, or aryl, where the alkyl and alkenyl are optionally interrupted with one or more oxygen or sulfur atoms. In some embodiments, L is $C_1$-$C_{10}$ alkylenyl and $X^1$ is absent. In some embodiments, L is $C_1$-$C_{10}$ alkylenyl and $X^1$ is oxo. In any of the above embodiments, $PG^1$ may be acrylyl, methacrylyl, epoxyl, isocycanyl, styrenyl, vinyl, oxyvinyl, thiovinyl, ketovinyl, ketoalkyl, ketoalkoxy, ketoaryl, or cycloalkenyl.

In some embodiments, $PG^1$ is —C(O)C($R^4$)=CH$_2$, —C(O)CH=CH$_2$, —O—CH=CH$_2$, —S—CH=CH$_2$, —N=C=O,

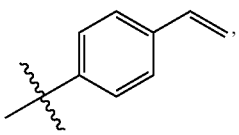 [SMILES: *c1ccc(C=C)cc1]

or

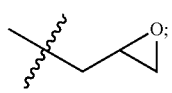

and $R^4$ is a $C_1$-$C_8$ alkyl. In certain embodiments, $PG^1$ is —C(O)C($R^4$)=CH$_2$ and $R^4$ is a $C_1$-$C_8$ alkyl. In other embodiments, $PG^1$ is —C(O)CH=CH$_2$. In one embodiment, $PG^1$ is —C(O)C($R^4$)=CH$_2$, $R^4$ is a $C_1$-$C_8$ alkyl, L is $C_1$-$C_8$ alkylenyl and X is absent.

Illustrative groups for $X^1$ include —NH—, —O—, —S—, and —PH—.

In other embodiments, $R^1$ is H and $R^2$ is H. In certain embodiments, $R^1$ is $C_1$-$C_6$ alkyl and $R^2$ is $C_1$-$C_6$ alkyl.

In other embodiments, L is $C_1$-$C_{10}$ alkylene.

In some embodiments, L is $C_1$-$C_{10}$ alkylenyl, $X^1$ is absent, and $R^1$ and $R^2$ are independently H or $C_1$-$C_6$ alkyl. In other embodiments, L is $C_1$-$C_{10}$ alkylenyl, $X^1$ is oxo, and $R^1$ and $R^2$ are independently H or $C_1$-$C_6$ alkyl.

The compound of Claim 1 may be a compound represented by Formula IA:

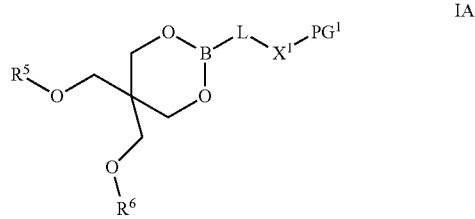

IA

In Formula IA, L may be absent, or alkylenyl, alkenylenyl, or arylene, where the alkylenyl and alkenylenyl are optionally interrupted with one or more oxygen or sulfur atoms; $X^1$ is absent, or is amino, oxo, thio, or phosphino; $PG^1$ is a polymerizable group, and $R^5$ and $R^6$ are independently H, alkyl, alkenyl, aryl, or —C(O)$R^7$; and $R^7$ is alkyl, alkenyl, or aryl. In certain embodiments, $R^5$ is —C(O)alkyl and $R^6$ is —C(O)alkyl. In other embodiments, $R^5$ is —C(O)($C_{15}$-$C_{20}$ alkyl) and $R^6$ is —C(O)($C_{15}$-$C_{20}$ alkyl). $PG^1$ may be a group of formula —C(O)C($R^4$)=CH$_2$, —C(O)CH=CH$_2$, —O—CH=CH$_2$, —S—CH=CH$_2$, —N=C=O,

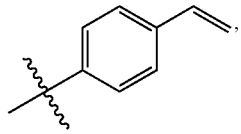 [SMILES: *c1ccc(C=C)cc1]

or

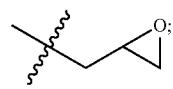

where $R^4$ is a $C_1$-$C_8$ alkyl. In certain embodiments, $PG^1$ is —C(O)C($R^4$)=CH$_2$ and $R^4$ is a $C_1$-$C_8$ alkyl. In other embodiments, $PG^1$ is —C(O)CH=CH$_2$. In one embodiment, $PG^1$ is —C(O)C($R^4$)=CH$_2$, and $R^4$ is a $C_1$-$C_8$ alkyl.

In certain embodiments, L is $C_1$-$C_{10}$ alkyl. In other embodiments, $X^1$ is —O—. In some embodiments, L is $C_1$-$C_{10}$ alkyl, $X^1$ is —O—, $R^5$ is —C(O)alkyl, and $R^6$ is —C(O)alkyl.

In another aspect, a polymer is provided that includes a polymerization product of the compound as represented by Formula I. In certain embodiments, the polymer has a weight average molecular weight of about 5,000 to about 2,000,000 g/mol. For example, the polymer may have a weight average molecular weight of about 100,000 to about 1,000,000 g/mol.

In yet another aspect, compositions are provided that include the compound as represented by Formula I and a cellulosic material. In certain embodiments, the composition includes cellulosic material that is wood, and the composition is a wood-polymer borinane composite material. For example, the composition may include an article such as, but not limited to, a railroad tie, a pole, or a building member.

In another aspect, a process is provided of preparing a wood-polymer borinane composite material, the process including contacting a cellulosic material with a compound represented by Formula I; and polymerizing the compound:

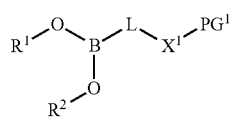

I to form the wood-polymer borinane composite material. The groups in Formula I are as described above. The contacting step may include employing a pressure process, a full cell process, or a fluctuation pressure process to impregnate the compound into the cellulosic material. For example, cellulosic materials such as woods typically are porous and the compounds may be forced into the porous structure by pressuring the system. Alternatively, a vacuum/pressurization process may be used, where a vacuum is drawn on the cellulosic material to withdraw some gases or low boiling point compounds from the cellulosic material and a subsequent pressurization forces the compound of Formula I into the cellulosic material.

The polymerizing step may also include activating the polymerizable group. For example, the activating of the polymerizable group may includes heating the polymerizable group, applying ultraviolet irradiation to the polymerizable group, adding a thermal initiator to the polymerizable group, or adding a photochemical initiator to the polymerizable group. Where the activating the polymerizable group includes adding a thermal initiator to the polymerizable group, the thermal initiator may include, but is not limited to, 4,4-azobis (4-cyanovaleric acid), 1,1'-azobis(cyclohexanecarbonitrile), 2,2'-azobisisobutyronitrile, benzoyl peroxide, tert-butyl peracetate, lauroyl peroxide, or dicumyl peroxide. Where the activating the polymerizable group includes adding a photochemical initiator to the polymerizable group, the initiator may include, but is not limited to, 3-butyl-2-[5-(1-butyl-3,3-dimethyl-1,3-dihydro-indol-2-ylidene)-penta-1,3-dienyl]-1,1-dimethyl-1H-benzo[e]indolium triphenylbutylborate, 3-butyl-2-[5-(3-butyl-1,1-dimethyl-1,3-dihydro-benzo[e]indol-2-ylidene)-penta-1,3-dienyl]-1,1-dimethyl-1H-benzo[e]indolium triphenylbutylborate, or 6-hydroxy-2,4,5,7-tetraiodo-3-oxo-9,9a-dihydro-3H-xanthene-9-carbonitrile. In some embodiments, the step of activating the polymerizable group includes heating the polymerizable group to a temperature of about 40° C. to about 120° C.

As noted above, a process for treating wood and wood products with the compound having a pendant dioxaborinane moiety is also provided. The methods may include applying a compound of Formula I, or a preservative solution thereof, into wood under a pressure regime to infuse the compound into the wood. Such methods of infusion may optionally further include the selective application of increased pressure or vacuum. In further embodiments, methods are provided that involve an additional step of polymerizing, in-situ, the compound of Formula I within the wood. Both steps, which are described more thoroughly below, can be conducted separately or simultaneously.

Before applying the preservative solution of a compound of Formula I, the wood may optionally be seasoned until a substantial fraction of free water has been removed from the cell spaces, with the resulting seasoned wood having its moisture content reduced by at least 25%, or at least 50%, or at least 75%, varying slightly with different species of wood. In certain embodiments, decreasing the moisture content of the wood creates more space to apply the preservative solution of a compound of Formula I into the wood, and decreases the likelihood that splits will develop in the applied wood. In certain embodiments, cutting, machining, and/or boring of the wood is conducted before the preservative solution of a compound of Formula I is applied.

The preservative solution of a compound of Formula I may be applied to wood by dipping, soaking, spraying, brushing, injecting, or any other well known means. The preservative solution of a compound of Formula I may be applied at ambient temperature, but advantageously, can also be heated to assist penetration of the compound into the wood. In certain embodiments, methods are provided in which the preservative solution of a compound of Formula I is applied to the wood by impregnating it into the wood. In still other embodiments, the preservative solution of a compound of Formula I is applied as a surface coat which is polymerized to encapsulate the wood.

On a weight to weight percent basis, the preservative solution of a compound of Formula I will be present in the final wood product in an amount of about 0.01 wt. % to about 10.0 wt. %. This may include from about 0.10 wt. % to about 3.0 wt. %, or from about 0.10 wt. % to about 2.0 wt. %, or from about 0.10 wt. % to about 1.0 wt. %, or from about 0.10 wt. % to about 0.50 wt. %, or from about 0.10 wt. % to about 0.30 wt. %. Specific examples of weight percent include about 0.01 wt. %, about 0.10 wt. %, about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, and ranges between any two of these values.

The wood may also be treated with one or more additives either before, after, or simultaneously upon treatment with the preservative solution of a compound of Formula I. These other additives may include solvents such as glycol-based solvents, water repellents, such as waxes, resins, or polymers, fire retardants, such as phosphates, mildewicides, insecticides, mouldicides, or pigments. One or more of these additives may be applied before the preservative solution of a compound of Formula I. One or more of these additives may be applied after the preservative solution of a compound of Formula I. In certain embodiments, one or more of these additives may be applied simultaneously with the preservative solution of a compound of Formula I.

A vacuum or decreased pressure can be applied to degas the wood sample and maximize pore sizes within the wood prior to the application of the preservative solution of a compound of Formula I. Vacuum and/or pressure techniques may also be used to impregnate the wood, including both the "Empty Cell" process and the "Full Cell" process, both of which are well known to those skilled in the art. In certain embodiments, existing processes are used to impregnate the wood with the preservative solution of a compound of Formula I, including the Bethell, Lowry, Reuping, and MSU processes.

The Bethell process involves using an initial vacuum to remove air from the wood cells and then flooding a cylinder loaded with the wood under vacuum with a preservative solution of a compound of Formula I. Positive pressure of, for example, about 1400 kPa is then applied for a predetermined time, the preservative solution of the compound of Formula I is drained and a final vacuum is drawn.

In the Lowry process, no initial vacuum is applied and the cylinder is flooded under atmospheric pressure with a preservative solution of a compound of Formula I. Positive pressure of, for example, about 1400 kPa is then applied for a predetermined period, the cylinder is then drained and a final vacuum drawn. The net uptake of the preservative solution of a compound of Formula I is lower because the air is not removed from the wood cells but is compressed during treatment, thus resulting in kickback of the preservative solution of a compound of Formula I when pressure is released and the timber evacuated.

The Reuping process involves applying an initial air pressure of, for example, about 350 kPa to the wood in the cylinder and then flooding the cylinder with a solution of the preservative solution of a compound of Formula I while holding this initial air pressure. Increased pressure of, for example, about 1000 kPa is then applied and, after a predetermined time, the pressure is released and the cylinder drained. A final vacuum is then drawn. This process has a lower net uptake of the preservative solution of a compound of Formula I than both the Bethell and Lowry processes.

The MSU process is a modification of the Reuping process. The Reuping process is carried out but the cylinder is drained while maintaining a pressure of, for example, about 300 kPa. Heat is then applied by steaming the wood. After the steaming period, kickback is allowed to occur by reducing the pressure and a final vacuum is drawn.

Depending on the degree of saturation that is desired, pre- and post-impregnation vacuum application may be employed or eliminated. In certain embodiments, the preservative solution of a compound of Formula I may be preheated to accelerate impregnation and to increase the level of penetration into the wood as well as to promote polymerization of the compound of Formula I during the impregnation process.

The polymerization prevents, or at least minimizes, later leaching of the compound of Formula I, and the preservative solution thereof, from the wood. Depending on the application and the potential detrimental effects of selected additives, it may be desirable to promote a greater degree of polymerization throughout the wood to fully solidify the compound of Formula I or it may be desired to allow the preservative solution of the compound of Formula I within the wood to remain slightly fluid. In certain embodiments, the method provides a polymerized solid surface coat of the preservative solution of the compound of Formula I.

In-situ polymerization of the compound of Formula I during and after impregnation of the wood can be promoted by conventional means. In certain embodiments, the in-situ polymerization includes activating the polymerizable group. In other embodiments, activating the polymerizable group includes heating, activating the polymerizable group with electromagnetic radiation, adding a thermal initiator, or adding a photochemical initiator. Electromagnetic radiation includes radiation from the electromagnetic spectrum having a wavelength from 0.1 angstrom (Å) to 1,000 meters (m). In certain embodiments, activating the polymerizable group includes activating the polymerizable group with ultraviolet (UV), visible, or near-infrared (IR) radiation. UV radiation has a wavelength from about 10 nm to about 390 nm. Visible radiation has a wavelength from about 390 nm to about 750 nm. Near-IR radiation has a wavelength from about 750 nm to about 3 µm. In certain embodiments, the in-situ polymerization is promoted through the application of heat. In certain embodiments, the in-situ polymerization is promoted by adding a thermal initiator.

The amount and duration of heat to be applied varies depending, for example, upon the size of the wood under treatment or the nature of the wood. As stated, in-situ polymerization of the compound of Formula I serves to fix the compound of Formula I within the wood, or at least increase the compound's viscosity within the wood, together with any additives from the preservative solution.

In certain embodiments, in-situ polymerization of the compound of Formula I is promoted through the application of UV radiation. In certain embodiments, in-situ polymerization of the compound of Formula I is promoted by adding a photochemical initiator.

In certain embodiments, methods are provided to surface treat the wood with a layer of the preservative solution of a compound of Formula I and polymerize the surface layer to encapsulate the wood. In other embodiments, the surface layer of the compound of Formula I is polymerized with the application of heat or ultraviolet radiation.

In another aspect, a method is provided of preparing a compound as represented by Formula I, the method including a first step of contacting a compound of Formula II with a compound of Formula III to form the compound of Formula I where Formula I is:

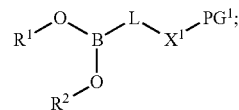

Formula II is:

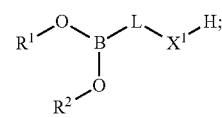

and

Formula III is $PG^1$-Y.

The variables for the compounds of Formula I and II are as described above for Formulas I and IA. In Formula III, $PG^1$ may be a group as described above and Y is a leaving group.

The present technology, thus generally described, will be understood more readily by reference to the following Examples, which are provided by way of illustration and are not intended to be limiting of the present technology.

EXAMPLES

Example 1

Synthesis of Acrylic-Dioxaborinane Wood Preservatives

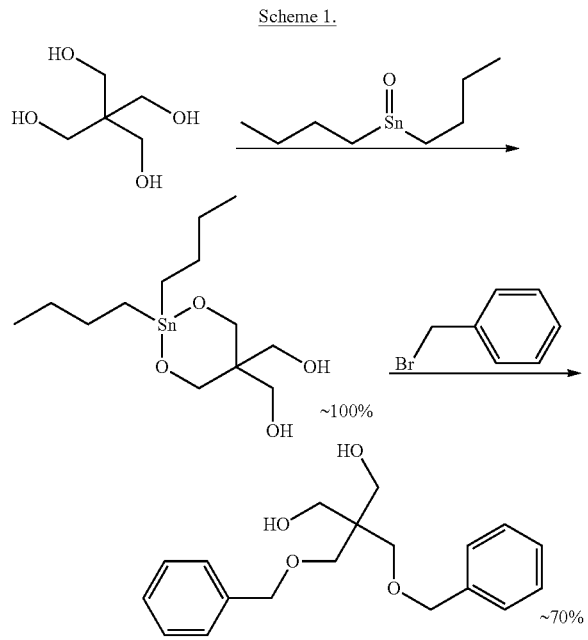

Scheme 1.

Step 1. Synthesis of Bis-Esters and Ethers of Pentaerythritol (Scheme 1)

2,2-Bis(benzyloxymethyl)-1,3-propanediol was prepared by combining pentaerythritol (10.36 g, 100 mmol) and dibutyltin oxide (50.00 g, 200 mmol) under reflux in methanol for four hours. The solvent was then removed by evaporation and the glassy residue was dried by keeping for 1 day at 40° C. under diminished pressure, and then by co-evaporation with toluene. The product was stored in a desiccator.

A suspension of the above stannylene derivative (6.00 g, 10 mmol) in toluene (100 mL) was combined with benzyl bromide (5.00 mL, 40 mmol) and tetraethyl ammonium bromide (270 mg), heated at reflux for four hours, cooled to room temperature, and stirred with water (200 mL). Evaporation of the organic phase gave a residue from which was separated, by chromatography (EtOAc) and recrystallization from petroleum ether, the crystalline dibenzyl ether (70%), mp 73° C., $^1$H NMR: 3.65 (4H); 3.58 (4H); 2.69 (2H); 4.83 (4H); 7.1-7.8 (10H).

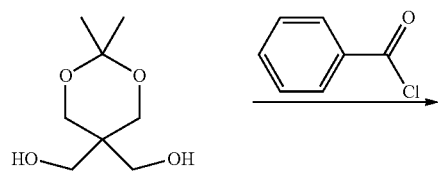

Scheme 2.

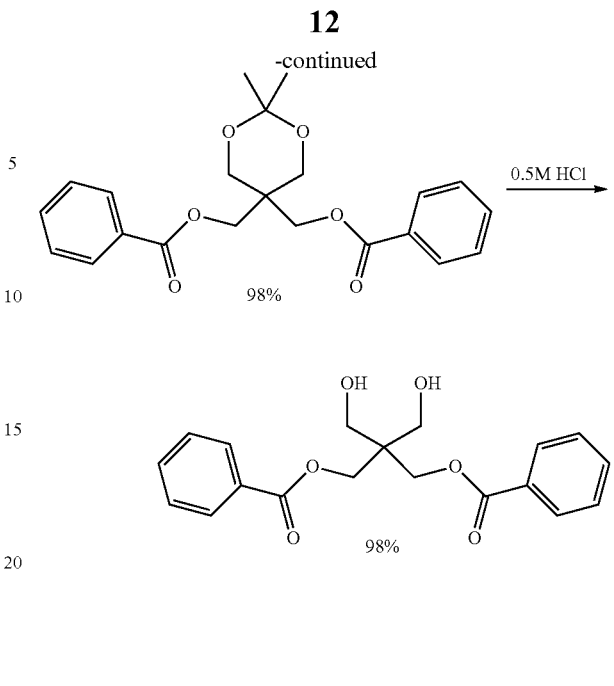

Synthesis of 2,2-bis(benzoyloxymethyl)-1,3-propanediol (Scheme 2)

To an anhydrous THF solution of 2,2-dimethyl-1,3-dioxane-5,5-dimethanol (100 mmol) and Et$_3$N (340 mmol) at 0° C. was added benzoic acid chloride (220 mmol; 1.1 equiv for each alcohol unit) dropwise over 30 min. The reaction was then allowed to warm to room temperature and was stirred for 15 hours. The crude reaction mixture was evaporated and then extracted from MeCl$_2$ (300 mL) and water (500 mL). The extraction was repeated with 2 portions of MeCl$_2$ (100 mL) followed by drying the combined organic layer over aqueous Na$_2$SO$_4$, filtering, and evaporating to yield the crude product. The crude benzoic acid, 4-(2,2-dimethyl-1-oxopropyl)-2,2-bis-(hydroxymethyl)-1,3-propanediyl ester, was purified by chromatography (1:1 petroleum ether:EtOAc) in 98% yield. mp 104-105° C.; $^1$H NMR: 2.76 (bs, 2H), 3.79 (s, 4H), 4.52 (s, 4H), 7.6-8.0 (10H).

Step 2. Synthesis of Acrylic-Dioxaborinane Wood Preservatives (Scheme 3)

To a three neck flask equipped with a Dean-Stark apparatus and under an inert argon atmosphere was added 13.4 g (78 mmol) of 3-boronic acid propyl methacrylate in toluene (50 mL). To the solution was added 24.7 g (78 mmol) of 2,2-bis(benzyloxymethyl)-1,3-propanediol and the solution was brought to reflux. Water formed from the reaction was collected by the Dean-Stark apparatus, which also served to monitor the progress of the reaction. The reaction typically took four hours to complete. The toluene was then removed by rotary evaporation, which left behind a viscous liquid. The liquid was then purified using EtOAc-hexanes (1:1) and yields were typically 90% or greater.

Scheme 3.

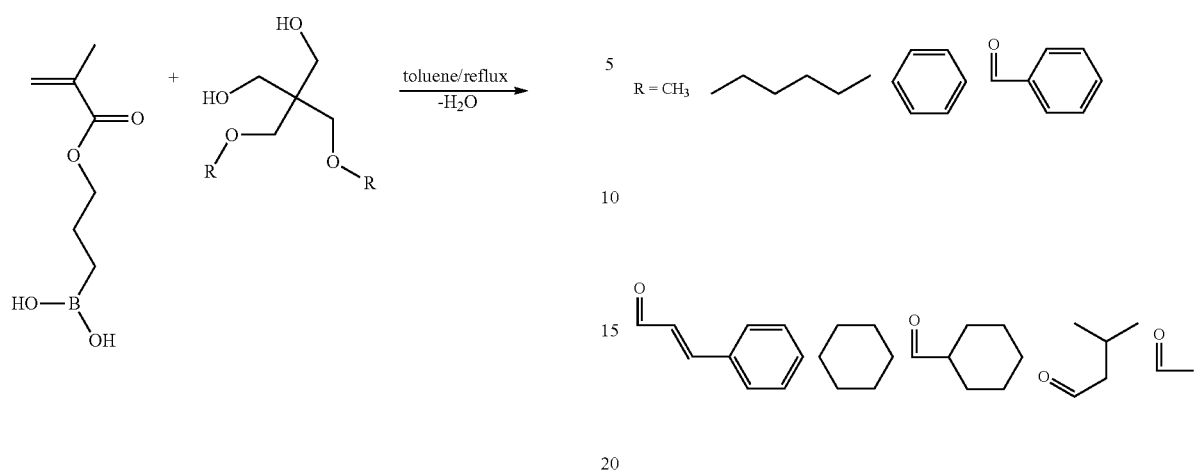

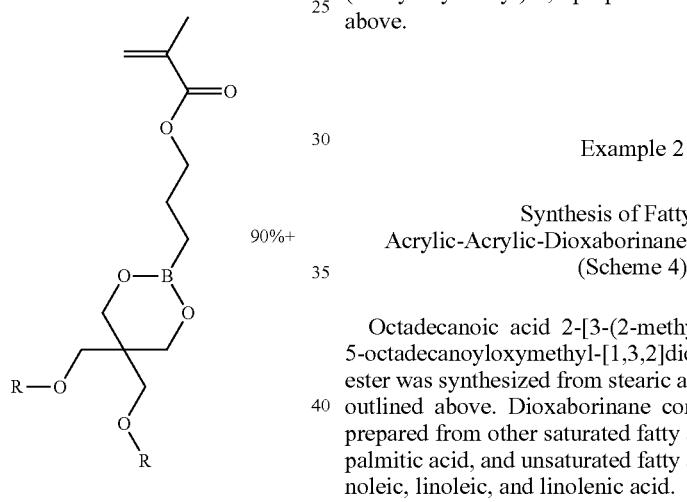

Each of the possible compounds of varying R groups may be prepared by substituting the appropriate diol for the 2,2-bis (benzyloxymethyl)-1,3-propanediol as described for Step 2, above.

Example 2

Synthesis of Fatty Acid Acrylic-Acrylic-Dioxaborinane Wood Preservatives (Scheme 4)

Octadecanoic acid 2-[3-(2-methyl-acryloyloxy)-propyl]-5-octadecanoyloxymethyl-[1,3,2]dioxaborinan-5-ylmethyl ester was synthesized from stearic acid using the procedures outlined above. Dioxaborinane compounds were likewise prepared from other saturated fatty acids, such as lauric and palmitic acid, and unsaturated fatty acids, such as oleic, ricinoleic, linoleic, and linolenic acid.

Scheme 4.

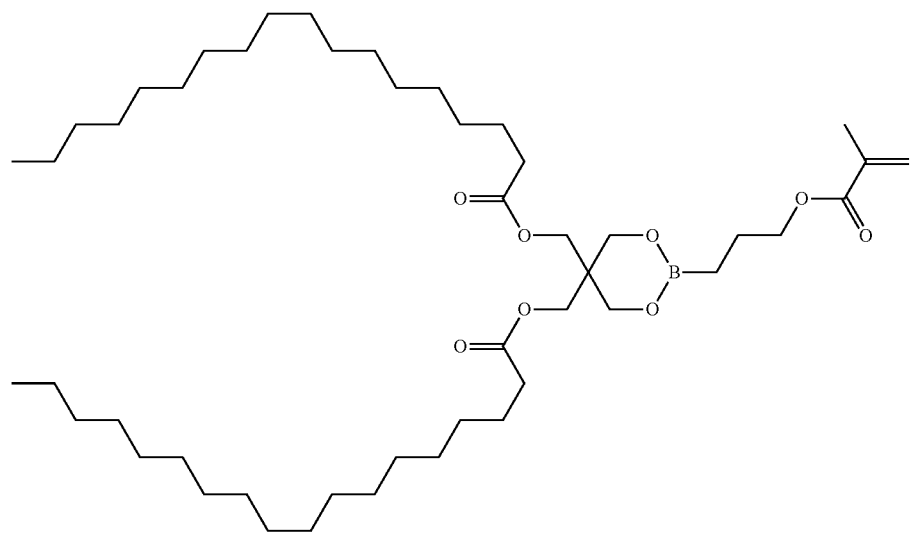

Example 3

Pressure Treatment Process

Pressure treatment ensures that the acrylic-dioxaborinanes completely impregnates the wood. The treatment of the wood is carried out in closed vessels where the wood is exposed to the acrylic-dioxaborinanes and then pressure and/or vacuum is applied. The acrylic-dioxaborinane penetrates deeply and uniformly into the wood. The conditions under which the acrylic-dioxaborinane is applied can be controlled to vary the degree to which the acrylic-dioxaborinane penetrates the wood and is retained. The pressure processes can be further adapted for large-scale protection of railroad ties, telephone poles, building members, and structural materials.

Example 4

Full-Cell Process

The full-cell process is used as a variation of the pressure treatment process. However, in the full-cell process it is preferable to keep as much of acrylic-dioxaborinane preservative absorbed into the wood during the pressure period as possible. The desired retention of the acrylic-dioxaborinane preservative is achieved by changing the concentration of the solution.

Example 5

Fluctuation Pressure Process

The fluctuation process is another variation of the pressure process. The fluctuation process is a "dynamic" process because the conditions under which the acrylic-dioxaborinane is applied are constantly changing. The pressure inside the preservative application cylinder changes between vacuum and high pressure within a few seconds in the fluctuation process. This process is used for woods that can split or otherwise fail under other pressure application procedures. Generally, as a result of this fluctuation process, penetration depths of the preservatives may be limited.

Example 6

Polymerization in Wood

The acrylic wood preservative was polymerized once it was within the wood structure (Scheme 5). This step fixed the wood preservative into the wood structure, preventing it from leaching out of the wood, and further served to strengthen the wood. This step is optional as the acrylic-dioxaborinane preservative can be used to preserve wood without polymerizing the preservative. The acrylic-dioxaborinane preservative was introduced into the wood structure by means of pressure, as described above, where it filled the fine grains and voids located within the wood. After the acrylic-dioxaborinane preservative was introduced into the wood structure, it was heated to 65-75° C., causing the acrylic-dioxaborinane preservative to polymerize into a solid form.

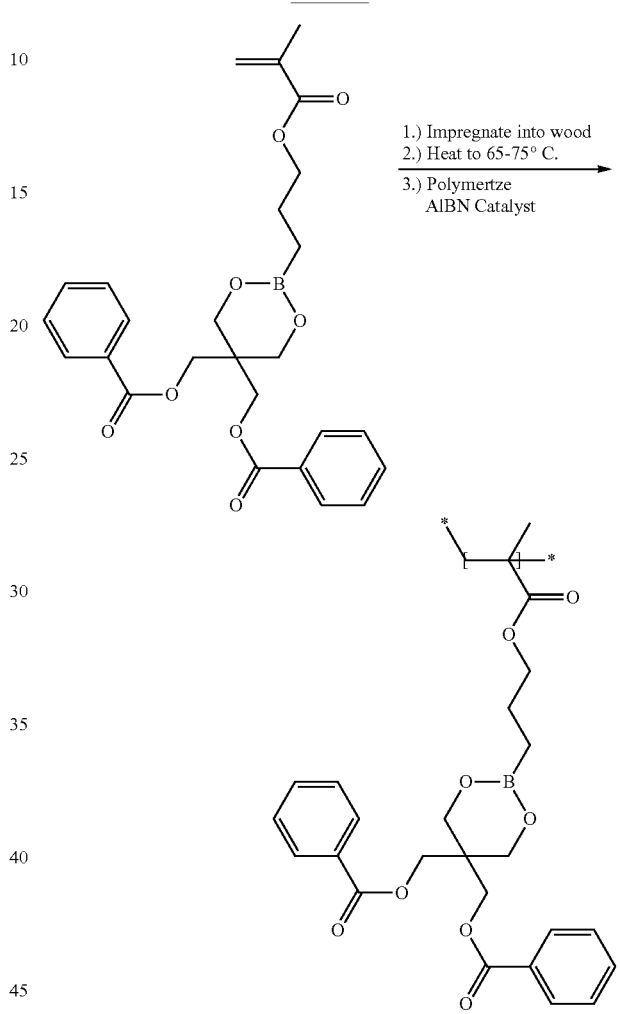

Scheme 5.

Once the acrylic-dioxaborinane preservative is polymerized within the wood structure it will not readily flow to the base of the wood structure and leak into the surrounding environment. Rather, the polymerized acrylic-dioxaborinane preservative will generally remain fixed throughout the treated wood structure and thereby persist within the wood structure for longer periods of time relative to existing liquid preservatives. Conversely, existing liquid preservatives can migrate from the wood structure into the surrounding environment, and leave the wood structure unprotected.

EQUIVALENTS

The embodiments, illustratively described herein may suitably be practiced in the absence of any element or elements, limitation or limitations, not specifically disclosed herein.

Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Similarly, the phrase "at least about" some value such as, e.g., wt % includes at least the value and about the value. For example "at least about 1 wt %" means "at least 1 wt % or about 1 wt %." Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

What is claimed is:

1. A compound of Formula IA:

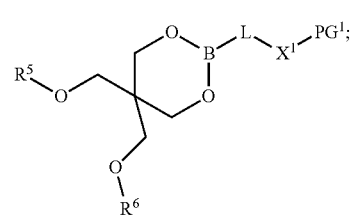

wherein:
L is absent, or is alkylenyl, alkenylenyl, or arylene, wherein the alkylenyl and alkenylenyl are optionally interrupted with one or more oxygen or sulfur atoms;
$X^1$ is absent, or is amino, oxo, thio, or phosphino;
$PG^1$ is a polymerizable group;
$R^5$ and $R^6$ are independently H, alkyl, alkenyl, aryl, or —C(O)R$^7$; and
$R^7$ is alkyl, alkenyl, or aryl.

2. The compound of claim 1, wherein $PG^1$ is acrylyl, methacrylyl, epoxyl, isocyanyl, styrenyl, vinyl, oxyvinyl, thiovinyl, ketovinyl, ketoalkyl, ketoalkoxy, ketoaryl, or cycloalkenyl.

3. The compound of claim 1, wherein $PG^1$ is —C(O)C(R$^4$)=CH$_2$, —C(O)CH=CH$_2$, —O—CH=CH$_2$, —S—CH=CH$_2$, —N=C=O,

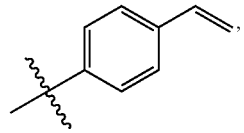 [SMILES: *c1ccc(C=C)cc1]

or

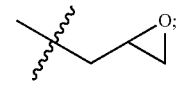

and $R^4$ is a $C_1$-$C_8$ alkyl.

4. The compound of claim 1, wherein $PG^1$ is —C(O)C(R$^4$)=CH$_2$ and $R^4$ is a $C_1$-$C_8$ alkyl.

5. The compound of claim 1, wherein $PG^1$ is —C(O)CH=CH$_2$.

6. The compound of claim 1, wherein $X^1$ is —NH—, —O—, —S—, or —PH—.

7. The compound of claim 1, wherein L is $C_1$-$C_{10}$ alkylene.

8. The compound of claim 1, wherein $R^5$ is —C(O)alkyl and $R^6$ is —C(O)alkyl.

9. The compound of claim 1, wherein $X^1$ is —O—.

10. A polymer comprising a polymerization product of the compound of claim 1.

11. A composition comprising the compound of claim 1 and a cellulosic material.

12. The composition of claim 11, wherein the cellulosic material is wood, and the composition is a wood-polymer borinane composite material.

13. A process of preparing a wood-polymer borinane composite material comprising:

contacting a cellulosic material with a compound of Formula IA; and
polymerizing the compound of Formula IA to form the wood-polymer borinane composite material;
wherein:
Formula IA is:

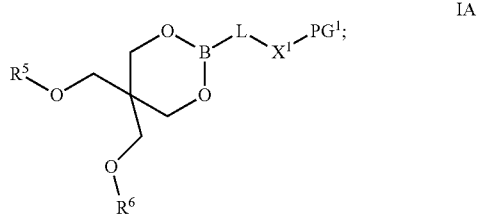

L is absent, or is alkylenyl, alkenylenyl, or arylene, wherein the alkylenyl and alkenylenyl are optionally interrupted with one or more oxygen or sulfur atoms;
$X^1$ is absent, or is amino oxo, thio, or phosphino;
$PG^1$ is a polymerizable group;
$R^5$ and $R^6$ are independently H, alkyl, alkenyl, aryl, or —C(O)$R^7$; and
$R^7$ is alkyl, alkenyl, or aryl.

14. The process of claim 13, wherein the contacting comprises employing a pressure process, a full cell process, or a fluctuation pressure process.

15. The process of claim 13, wherein the polymerizing comprises-activating the polymerizable group with UV, visible, or near-IR radiation, adding a thermal initiator to the polymerizable group, or adding a photochemical initiator to the polymerizable group.

16. The process of claim 13, wherein the polymerizing comprises adding a thermal initiator that is 4,4-azobis(4-cyanovaleric acid), 1,1'-azobis(cyclohexanecarbonitrile), 2,2'-azobisisobutyronitrile, benzoyl peroxide, tert-butyl peracetate, lauroyl peroxide, or dicumyl peroxide, or adding a photochemical initiator to the polymerizable group that is 3-butyl-2-[5-(1-butyl-3,3-dimethyl-1,3-dihydro-indol-2-ylidene)-penta-1,3-dienyl]-1,1-dimethyl-1H-benzo[e]indolium triphenylbutylborate, 3-butyl-2-[5-(3-butyl-1,1-dimethyl-1,3-dihydro-benzo[e]indol-2-ylidene)-penta-1,3-dienyl]-1,1-dimethyl-1H-benzo[e]indolium triphenylbutylborate, or 6-hydroxy-2,4,5,7-tetraiodo-3-oxo-9,9a-dihydro-3H-xanthene-9-carbonitrile.

17. An article comprising the composition of claim 12.

18. The article of claim 17 which is a railroad tie, a pole for supporting cable, or a building member.

19. A method of preparing a compound of Formula IA, the method comprising:
contacting a precursor compound with a compound of Formula III to form the compound of Formula IA;
wherein:
Formula IA is:

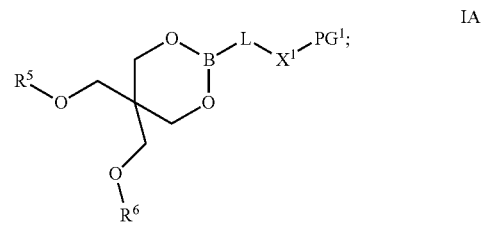

the precursor compound is:

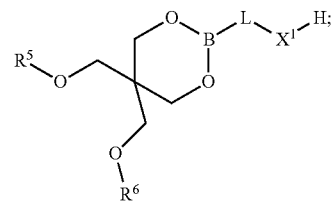

Formula III is $PG^1$-Y;
L is absent, or is alkylenyl, alkenylenyl, or arylene, wherein the alkylenyl and alkenylenyl are optionally interrupted with one or more oxygen or sulfur atoms;
$X^1$ is absent, or is —O—, —NH—, —S—, or —P($R^3$)—;
$R^5$ and $R^6$ are independently H, alkyl, alkenyl, aryl, or —C(O)$R^7$;
$R^7$ is alkyl, alkenyl, or aryl
$PG^1$ is acrylyl, methacrylyl, epoxyl, isocycanyl, styrenyl, vinyl, oxyvinyl, thiovinyl, ketovinyl, ketoalkyl, ketoalkoxy, ketoaryl, or cycloalkenyl; and
Y is a leaving group.

* * * * *